United States Patent [19]

Leclerc et al.

[11] Patent Number: 4,766,151

[45] Date of Patent: Aug. 23, 1988

[54] ETHERS AND OXIME ETHERS OF ALKYLAMINO ALCOHOLS AS MEDICAMENTS AND NOVEL PRODUCTS, AND PROCESSES FOR THEIR PREPARATION

[75] Inventors: Gérard Leclerc; Mohammed Bouzoubaa, both of Strasbourg; Guy Andermann, Colmar; Georges de Burlet, Beblenheim; Catherine Cannet, Colmar; Jacques Himber, Guebwiller, all of France

[73] Assignee: Laboratoires, P.O.S., Kaysersberg, France

[21] Appl. No.: 788,694

[22] Filed: Oct. 21, 1985

Related U.S. Application Data

[63] Continuation of Ser. No. 467,262, Feb. 17, 1983, abandoned.

[30] Foreign Application Priority Data

Feb. 19, 1982 [FR] France ................. 82 02740

[51] Int. Cl.$^4$ ............... C07C 131/02; C07C 131/04; A61K 31/15
[52] U.S. Cl. ..................... 514/640; 514/579; 514/913; 564/1; 564/256; 564/462
[58] Field of Search ............. 564/256; 514/640, 913

[56] References Cited

FOREIGN PATENT DOCUMENTS 0037777  4/1981  European Pat. Off. .

OTHER PUBLICATIONS

Leclerc, G. *J. Med. Chem.* vol. 23 (1980) pp. 620–624.
Goodman and Gilman *The Pharmacological Basis of Therapeutics* 6th Ed. (1980) at p. 195, MacMillan Publ. Co.

*Primary Examiner*—Michael L. Shippen
*Attorney, Agent, or Firm*—Mason, Fenwick & Lawrence

[57] ABSTRACT

Glaucoma can be treated by the application to the eye of a physiologically active amount of a compound of the formula

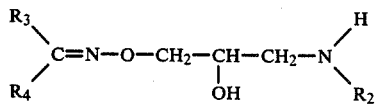

in which:
  each of $R_3$ and $R_4$ is selected from hydrogen, and alkyl, alkenyl and cycloalkyl radicals, or $R_3$ and $R_4$ together with the carbon between them are a cycloalkylidene radical,
  $R_2$ is a lower alkyl radical, and the salts thereof with pharmaceutically acceptable acids, in an opthamologically accepted carrier therefor, which when liquid and an isotonic agent is present can have the form of an eye lotion. The 1-N-tert.-butylamino derivatives of 3-(cyclopropyl-methyl-ketone-oximino)-propan-2-ol, 3-(dicyclopropyl-ketone-oximino)-propan-2-ol, and 3-(3,3,5-trimethylcyclohexane-1-ketone-oximino)-propan-2-ol are novel compounds within such formula specifically useful for such treatment.

16 Claims, No Drawings

ETHERS AND OXIME ETHERS OF ALKYLAMINO ALCOHOLS AS MEDICAMENTS AND NOVEL PRODUCTS, AND PROCESSES FOR THEIR PREPARATION

This is a continuation of application Ser. No. 467,262, filed Feb. 17, 1983, now abandoned.

The present inventin relates to the field of medicaments. It concerns ethers or oxime-ethers of alkylaminoalcohols as active ingredients of medicinal compositions intended especially for the treatment of diseases of the eye, especially glaucoma, and cardiovascular diseases.

The beta-blocking activity and anti-hypertensive properties of aromatic ortho-amino-oximes of the general formula: $A=N-O-CH_2-CHOH-CH_2NH-R$, in which R is an aliphatic radical whilst A is a radical containing at least one aromatic nucleus has already been reported (French Pat. No. 76/03,282 of Feb. 6, 1976). However, if such derivaties or their pharmaceutically acceptable salts, for example timolol maleate, are used in the treatment of glaucomas, undesirable secondary effects are frequently noted, such as, in particular, bronchial disorders (asthma) or cardiovascular disorders (orthostatic hypotension and slowing down of the pulse rate).

Moreover there are known, as chemical products, ortho-amino-oximes in whch the radical A in the above formula can be aliphatic (G. Leclerc et al., J. Med. Chem. 23, 6, p. 620-624, 1980). However, no therapeutic application whatsoever, especially as a medicament, and hence no application in the ophthalmological field, has been reported and studied for such products.

Finally, alkoxypropanolamines of the formula $R_1-O-CH_2-CHOH-CH_2-NH-R$, in which $R_1$ is an alkyl, alkenyl or alkinyl radical, are known. These compounds are presented in European patent application No. 0,037,780 as having a beta-blocking activity which is useful in the treatment of cardiovascular disorders, but they cannot be used in therapeutic application to the eye, because of their poor local tolerance and their anaesthetic action, which is a major disadvantage for an eye lotion intended for the treatment of glaucoma.

It has now been found that certain aliphatic amino-oximes exhibit remarkable anti-hypertensive and anti-glaucomatous properties, without secondary consequences of their use, such as are encountered in the case of homologous products.

It has moreover been found that certain ethers of alkylaminoaliphatic derivatives of the same group as above also possess the same properties, with lower toxicity and lesser secondary effects than the oxime-ethers containing aromatic radicals.

The present invention thus relates, by way of novel medicaments, to the compounds corresponding to the general formula $$R_1-O-CH_2-CHOH-CH_2-NH-R_2 \quad (I)$$

in which:

$R_1$ is chosen from the group consisting of:
(a) a cycloalkyl radical or
(b) a group of the type

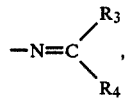

at least one of the radicals $R_3$ and $R_4$ being an alkyl, alkenyl or cycloalkyl radical or a hydrogen atom, and the radicals $R_3$ and $R_4$ being capable of jointly forming a cycloalkyl chain, and $R_2$ consists of a linear or branched lower alkyl radical ($C_1$ to $C_5$).

Thus, the compounds which can be used according to the invention can be considered either as ethers (case a) or as oxime-ethers (case b) of aliphatic aminoalcohols.

In practice, by way of non-limiting examples, there may be mentioned, as products falling within the above-mentioned scope, compounds in which $R_2$ is an ethyl, propyl or, preferably, isopropyl or tertiary butyl radical, $R_1$ is cycloalkyl, for example (cyclopropyl)$_2$—CH— or cyclopropyl—CH$_2$—, $R_3$ or $R_4$ in particular consists of a linear, branched or cyclic alkyl or together constitute an alkylidene radical having 2 or 10 carbon atoms, such as, for example, $CH_3-(CH_2)_4-CH=$, $CH_3-(CH_2(_2-C(CH_3)_2$, $(CH_3)_2C=$, $CH_3-(CH_2)_2-CH(CH_3)-CH_2-CH=$, $CH_3-CH=C(CH_3)-CH=$, $CH_3(CH_2)_8-CH=$, (cyclopropyl)$_2-C=$, (cyclopropyl)C(CH$_3$)=, etc., and $R_3$ and $R_4$ can jointly form a cyclohexane or 3,3,5-trimethylcyclohexane ring.

The invention moreover relates to any pharmaceutical composition which contains, as the active principle, at least one compound of the above formula (I).

The invention also relates, by way of novel chemical products, to the compounds of the above general formula (I) in which:

$R_1$ is chosen from the group consisting of:
(a) a cycloalkyl radical,
(b) a group of the type

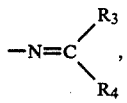

at least one of the radicals $R_3$ or $R_4$ being a cycloalkyl radical and the other radical being chosen from the group comprising the alkyl, alkenyl and cycloalkyl radicals and a hydrogen atom, and $R_3$ and $R_4$ can jointly form a cycloalkyl chain, as well as their salts with pharmaceutically acceptable acids.

The invention also relates to a process for the preparation of the compounds of the formula (I).

If $R_1$ is a cycloalkyl radical, the alcohol $R_1$—OH is reacted with an epihalohydrin to give a compound of the formula

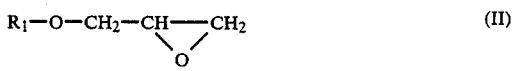

the compound of the formula (II) reacting with an amine of the formula $R_2$—$NH_2$ to give the compound of the formula (I), $R_2$ having the same meanings as above.

If R is the group of the type

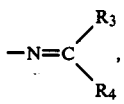

the ketone of the formula

is reacted with hydroxylamine to give the compound of the formula (III):

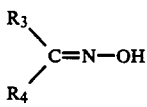 (III)

which, by reaction with an epihalohydrin, gives the compound of the formula (IV):

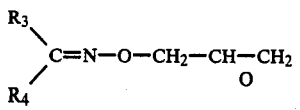 (IV)

which, by reaction with an amine $R_2$—$NH_2$, gives the compound (I), $R_2$, $R_3$ and $R_4$ having the same meanings as above.

EXPERIMENTAL SECTION

The following compounds, in particular, have been synthesised:

1-N-tert.-Butylamino-3-(cyclopropyl-methylketoneoximino)-propan-2-ol (in the form of the oxalate): compound No. 1.

1-N-tert.-Butylamino-3-(dicyclopropyl-ketoneoximino)-propan-2-ol (in the form of the fumarate): compound No. 2.

1-N-tert.-Butylamino-3-cyclopropylmethoxy-propan-2-ol (in the form of the maleate): compound No. 3.

1-N-tert.-Butylamino-3-dicyclopropylmethoxy-propan-2-ol (in the form of the fumarate): compound No. 4.

1-N-tert.-Butylamino-3-(3,3,5-trimethyl-cyclohexane-1-oximino)-propan-2-ol (in the form of the oxalate): compound No. 5.

1-N-tert.-Butylamino-3-cyclopropylethoxy-propan-2-ol (in the form of the oxalate): compound no. 6.

The essential properties of these compounds are shown in Table 1 below.

Compound No. 1 was synthesised in its two optical isomer forms S(−) and R(+), having the following characteristics:

S(−): optical rotation: $\alpha_D^{20°} = -3.3°$; melting point $=133°$ C.

R(+): optical rotation: $\alpha_D^{20°} = +2.7°$ melting point $=130°$ C. (approx.)

The invention also relates to the stereospecific syn and anti enantiomers.

TABLE 1

| Compound No | Base | Acid | Melting Point °C. F °C. | Calculated (%) C | H | N | Found (%) C | H | N | Yield % | Recrystallisation solvent |
|---|---|---|---|---|---|---|---|---|---|---|---|
| 1 | (structure: t-Bu-NH-CH₂-CH(OH)-CH₂-O-N=C(CH₃)-cyclopropyl) | COOH–COOH | hemioxalate 174 / oxalate 128 | 57,12 / 51,81 | 9,12 / 8,23 | 10,28 / 8,80 | 56,86 / 52,63 | 9,35 / 8,11 | 10,2 / 8,63 | 27 / 27 | AcOEt/MeOH / AcOEt/MeOH |
| 2 | (structure with dicyclopropyl ketoxime ether) | HOOC–CH=CH–COOH (fumaric) | 159 | 61,56 | 9,04 | 9,00 | 61,47 | 9,14 | 9,00 | 15 | AcOEt |
| 3 | (structure: t-Bu-NH-CH₂-CH(OH)-CH₂-O-CH₂-cyclopropyl) | COOH–COOH | 125 | 56,76 | 8,58 | 4,31 | 56,60 | 8,59 | 4,61 | 6,8 | AcOEt |
| 4 | (structure with dicyclopropylmethyl ether) | HOOC–CH=CH–COOH | 112 | 60,48 | 8,74 | 3,92 | 60,18 | 8,80 | 3,9 | 9 | AcOEt |
| 5 | (structure with 4,4-dimethylcyclohexanone oxime ether) | COOH–COOH | 88 | 57,73 | 9,15 | 7,48 | 57,65 | 9,17 | n.c. | 20 | Benzene/ Oxyde d'isopropyle |
| 6 | (structure: t-Bu-NH-CH₂-CH(OH)-CH₂-O-CH₂-cyclopropyl) | COOH–COOH | 116 | 55,04 | 8,94 | 4,59 | 54,88 | 8,97 | n.c. | 22 | AcOEt |

Some examples are given below.

I. Preparation of the maleate of 1-N-tert.-butylamino-3-cyclopropylmethoxy-propan-2-ol (compound No. 3)

Sodium cyclopropylmethylate is prepared from 10 g of cyclopropylmethanol (0.139 ml), 3.34 g (0.139 mol) of sodium hydride and 200 ml of anhydrous tetrahydrofuran; the sodium hydride must be added a little at a time; the reaction is complete when the evolution of hydrogen ceases. A solution of epibromohydrin-tetrahydrofuran (11.5 cc of epibromohydrin in 20 cc of THF) is added dropwise to the preceding solution, which has beforehand been cooled in an ice bath; after the addition, the mixture is stirred at ambient temperature for 48 hours. The sodium bromide formed is filtered off, the THF is evaporated, and the crude epoxide obtained is dissolved in absolute ethanol. 29.5 cc of tert.-butylmine (0.278 mol) are added to this latter solution; stirring is carried out at ambient temperature for 24 hours. The ethanol is evaporated under reduced pressure, the residue obtained is dissolved in ethyl acetate and the solution is dried over $MgSO_4$ and filtered. 0.139 mol of maleic acid is added to the filtrate. The salt formed is filtered off and recrystallised from ethyl acetate. Overall yield, based on the starting alcohol: 20%.

Compound No. 4 was prepared in the same manner, as was compound No. 6.

II. Preparation of the oxalate of 1-N-tert.-butylamino-3-(cyclopropyl-methyl-ketone-oximino)-propan-2-ol (compound No. 1)

The oxime is prepared from 4.5 g (0.05 mol) of cyclopropyl methyl ketone, 7 g of hydroxylamine hydrochloride (0.05×2 mols) and 8.2 g (0.05×2 mols) of sodium acetate, which are beforehand dissolved in 30 cc of distilled water. The mixture is stirred at 40° C. for 12 hours and extracted twice with AcOEt, the solvent is evaporated in a waterpump vacuum (slight heating <30° C.), the residue is taken up in a minimum amount of water, the acetic acid formed in the reaction is neutralised with potassium bicarbonate, the mixture is extracted twice with ethyl acetate, the extract is dried over $MgSO_4$ and filtered and the ethyl acetate is evaporated; the oxime obtained is pure; yield 88% (4.7 g of crude oxime). The oxime is dissolved in 100 ml of anhydrous THF, and 0.05 mol of NaH is added a little at a time. 3.9 cc of epibromohydrin dissolved in 10 cc of anhydrous THF are then added to the solution of the oxime salt which has beforehand been cooled in an ice bath; after addition in the cold, the mixture is stirred for 48 hours at ambient temperature, the sodium bromide formed is filtered off, the THF is evaporated under a waterpump vacuum, the crude epoxide is dissolved in absolute EtOH, (5.2×2) cc of tert.-butylamine are added, the mixture is stirred at ambient temperature for 24 hours, the ethanol is evaporated, the crude base is dissolved in a minimum amount of a 1N hydrochloric acid solution, the neutral and acidic impurities are extracted twice with ether, the aqueous phase is neutralised with $K_2CO_3$, the same solution is then saturated with $K_2CO_3$ and extracted three times with AcOEt, the extract is dried over $MgSO_4$ and filtered, and the AcOEt is evaporated. The crude base is dissolved in a minimum of AcOEt/ether (95/5), 6.30 g of oxalic acid dissolved in a minimum amount of AcOEt are added, and the oxalate formed is filtered off and recrystallised from an 80/20 AcOEt/MeOH mixture. 4.3 g of oxalate are recovered after drying under pump suction at a pressure of 0.01 mm Hg for two hours. Total yield of the reaction: 27%.

Compound No. 2 was prepared in the same manner.

III. Preparation of the oxalate of 1-N-tert.-butylamino-3-(3,3,5-trimethyl-cyclohexane-1-oximino)-propan-2-ol (compound No. 5)

The oxime is prepared from 10 g (0.07 mol) of 3,3,5-trimethylcyclohexanone, 0.07×2 mols of hydroxylamine hydrochloride, and 0.07×2 mols of sodium acetate, preferably dissolved in a minimum amount of distilled water. The mixture is stirred for 2 hours at 40° C. and cooled, and the oxime is filtered off and washed with 3×5 ml of water. The oxime is redissolved in ethyl acetate and the solution is dried over $MgSO_4$, filtered and evaporated to dryness. Yield 90%. The oxime obtained is dissolved in 100–200 cc of anhydrous THF, and NaOH (0.063 mol) is added in small amounts; the sodium salt is formed. A solution of 0.063 mol of epibromohydrin in THF is added dropwise to the solution of the oxime salt which has beforehand been cooled to an ice bath; after addition the mixture is stirred for 48 hours at ambient temperature. The sodium bromide formed is filtered off and the THF is evaporated. The crude epoxide is dissolved in absolute ethanol, 2×0.063 mol of tert.-butylamine are added, the mixture is stirred at ambient temperature for 24 hours and the ethanol and excess tert.-butylamine are evaporated. The crude base is dissolved in a minimum amount of 1N hydrochloric acid solution, the neutral and acidic impurities are extracted twice with ether, the aqueous phase is neutralised with $K_2CO_3$, the same solution is saturated with $K_2CO_3$ and extracred three times with AcOEt, the extract is dried over $MgSO_4$ and filtered, and the solvent is evaporated. The crude base (0.032 mol) is dissolved in a minimum amount of a 95/5 AcOEt/ether mixture and 0.032 mol of oxalic acid dissolved in AcOEt are added. The oxalate is filtered off and recrystallised from an AcOEt/isopropyl ether mixture. Overall yield of the synthesis: 20%.

Medicaments based on the abovementioned products and intended for local administration in the form of aqueous solutions, eye lotions, aqueous suspensions and ophthalmic ointments have proved very efficient as anti-hypertensive and anti-glaucomatous agents, in particular in the treatment of glaucomas where the intraoccular pressure is greater than 22 mm of mercury. Series of experiments and observations, in the toxicological, pharmacological and therapeutic field, carried out on eye lotions prepared according to the invention and containing 0.1 to 1% by weight of active agent have given very interesting results.

A. TOXICOLOGY:

Experiments on oral and intraperitoneal administration to mice and rats have shown a complete absence of acute toxicity and a 50% lethal dose LD 50 markedly greater to the maximum doses used for administration. The cytogenetic test for mutagenesis (or micronucleus test) has proved negative in rats. Moreover, the occular irritation index is virtually zero in rabbits and it has been possible to conclude that the products are very well tolerated by the human eye.

B. PHARMACOLOGY—PHARMACEUTICAL APPLICATIONS.

The results of experiments on rabbits have been highly significant. Experiments to measure the degree of allergenicity (Magnusson test), carried out on guinea pigs, have shown that no allergic phenomena whatsoever arise.

Moreover, mutagenic activity experiments on various bacteria have allowed the conclusion that the substances according to the invention are devoid of mutagenic power.

Finally, numerous multicentre studies carried out on man have demonstrated the great effectiveness of the medicaments of the invention.

In practice, the compositions according to the invention are particularly appropriate for use as eye lotions. In addition to the active constituent (or mixture) chosen from the abovementioned class of the formula (I), the eye lotion can contain various other constituents which perform various functions and which in particular play the following roles: isotonic agents, such as, for example, sodium chloride or potassium chloride; buffers, such as, for example, sodium or potassium phosphates and sodium borate; and, optionally, preservatives, such as, for example, non-toxic mercury salts, quaternary ammonium salts and chlorohexidine salts. Of course, as in the case of other eye lotions, the compositions are diluted by means of distilled water.

The usual dose, which varies according to the subject to be treated and to the medical condition in question, can be, for example, from 1 to 4 applications per day of an eye lotion containing from 0.1% to 1% of active principle, in man.

By way of a non-limiting example of the properties and application of compositions according to the invention there are indicated below the summarised results of the pharmacological study of the anti-glaucomatous activity, carried out on albino rabbits with various eye lotions according to the invention, in comparison with eye lotions containing the same concentrations of aromatic ethers of aminoalcohols of a known type, especially timolol maleate, of the following formula:

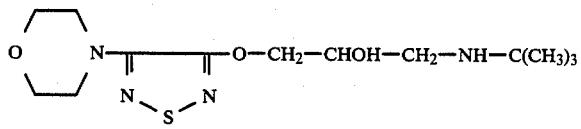

Certain eye lotions on which experiments were carried out according to the invention had the following composition:

| active agent | 0.1 to 1 g % |
|---|---|
| creatinine | 0.5 g % |
| citric acid | 0.5 g % |
| sodium chloride | 0.225 g % |
| hydroxyethylcellulose | 0.2 g % |
| sodium carbonate in an amount to give | pH 7.3 |
| purified water, q.s.p. to give | 100 ml |

Another composition which can be used has, for example, the following composition in % by weight:

| active agent | 0.5 |
|---|---|
| KH$_2$PO$_4$ | 0.113 |
| K$_2$HPO$_4$ | 0.95 |
| sodium chloride | 0.63 |
| benzalkonium chloride | 0.01 |
| purified water, q.s.p | 100 ml. |

Amongst the active agents of the formula (I) experiments were carried out, inter alia, on the products in which:

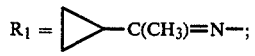

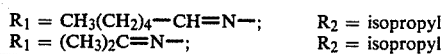

and more especially the above compounds 1 to 6, the doses of active agent in the eye lotion being 0.1%, 0.25%, 0.50% and 1% (by weight of the eye lotion).

In animals, the experiments were carried out on series of New Zealand albino rabbits weighing 3.5 to 4.5 kg and carrying out a double-blind experiment with each of the above dilutions, therapeutic rest being allowed between the treatments. Measurements without treatment were also carried out for sublocal anaesthesia of the eye of the rabbits with posicaine was employed so as to be able to follow the change in the I.O.P. (intraoccular pressure) in the animals.

A glaucoma was induced in the right eyes of the rabbits by intra-occular injection of alpha-chymotrypsin by the method of SEARS (Am. J. Ophthalmol. 1974, 71, p. 378) modified by VAREILLES et al. (Am. J. Ophthalmol. 1979, 2, 10, p. 561).

The I.O.P. values were measured every half hour over the first three hours and then every hour up to the 7th hour. In parallel, the local anaesthesia effect was measured, each measurement being carried out on both eyes at the same time, with the untreated left eye serving as a comparison test.

Not all the results obtained are given here in every detail, but they can be summarised as follows:

For virtually all the eye lotion compositions according to the invention, containing any one of the abovementioned active agents, the efficiency obtained is greater than that of the timolol derivatives, at equal concentrations, in respect of the anti-glaucomatous activity; this is covered with a vary rapid action. On average, for the active agents, with I.O.P. passed through a minimum three hours after instillation and did not revert to its initial value after a time of seven hours.

The anaesthetic effect produced by the various compositions on the rabbit cornea was generally zero for the compositions of the invention.

The hypotensive action did not vary significantly with concentration over all the products on which experiments were carried out.

The efficiency of the active products according to the invention pass through a maximum for the various concentrations mentioned above, the optimum dose being 0.1%, 0.25% or even 0.50%, depending on the particular case (the % being relative to the total weight of the eye lotion).

The beta-blocking activity was demonstrated by measuring the PA$_2$ values.

The PA$_2$ is the co-logarithm of the concentration of antagonist in the presence of which it requires twice as much agonist as in its absence in order to achieve the same effect; see, on this subject: Calculation of the PAx, Technical Leaflet No. 16, J. Pharmacol. Paris 1971, 2, 3, 373–380.

The PA$_2$ was measured on the isolated auricle of a guinea pig and on the isolated trachea of a guinea pig.

The results are summarised in Table 2 below. The product used by way of comparison is the following compound:

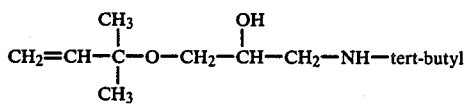

This compound is of the type which forms the subject of European patent application No. 0,037,780.

TABLE 2

| Compound No. | AURICLE OF THE GUINEA PIG | | TRACHEA pA$_2$ |
|---|---|---|---|
| | Chronotropic pA$_2$ | Inotropic pA$_2$ | |
| 1 | 8.7 | 9.0 | 9.04 |
| 2 | 8.3 | 8.14 | 8.67 |
| 3 | 7.1 | 6.7 | 6.23 |
| 4 | 4.83 | 4.50 | 4.51 |
| Comparison | 4.43 | 4.32 | 4.96 |

In man, the study of the action of the normal intraocular pressure has shown that the medicaments tested caused the intra-occular pressure to drop rapidly after instillation of a single drop of the eye lotion. In patients suffering from chronic open-angle glaucoma, the mean drop in pressure was 13 to 16 mm Hg on one instillation of eye lotion containing 0.5% of active principle.

In clincal tests it proved impossible to demonstrate secondary effects such as, for example, bronchial or cardiovascular disturbances (orthostatic hypotension, or slowing down of the pulse) which are found following the use of ethers or oxime-ethers of a structure close to that of the products of the invention and more generally of the aromatic beta-blocking agents of the prior art.

We claim:

1. 1-N-tert.-butylamino-3-(cyclopropyl-methyl-ketone-oximino)-propan-2-ol.

2. Composition for the treatment of glaucoma characterized in that it contains as an active ingredient the compound of claim 1, in proportion of 0.1 to 1% by weight, with an opthalmologically acceptable liquid vehicle, and an isotonic agent.

3. Process for the treatment of glaucoma, comprising applying to the eye of the patient a composition according to claim 2.

4. 1-N-tert.-butylamino-3-(di-cyclopropyl-ketone-oximino)-propan-2-ol.

5. Composition for the treatment of glaucoma characterized in that it contains as an active ingredient the compound of claim 4 in proportion of 0.1 to 1% by weight, with an opthalmologically acceptable liquid vehicle, and an isotonic agent.

6. Process for the treatment of glaucoma, comprising applying to the eye of the patient a composition according to claim 5.

7. 1-N-tert.-butylamino-3-(3,3,5-trimethyl-cyclo-hexane-1-ketone-oximino)-propan-2-ol.

8. Composition for the treatment of glaucoma characterized in that it contains as an active ingredient the compound of claim 7 in proportion of 0.1 to 1% by weight, with opthalmologically acceptable liquid vehicle, and an isotonic agent.

9. Process for the treatment of glaucoma, comprising applying to the eye of the patient a composition according to claim 8.

10. A pharmaceutical composition for the treatment of glaucoma comprising a physiologically active amount of a compound of the formula

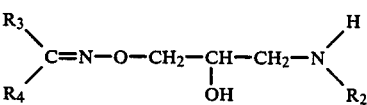

in which:
each of R$_3$ and R$_4$ is selected from hydrogen, and alkyl, alkenyl and cycloalkyl radicals, or R$_3$ and R$_4$ together with the carbon between them are a cycloalkylidene radical,
R$_2$ is a lower alkyl radical, and the salts thereof with pharmaceutically acceptable acids, and an opthamologically accepted carrier therefor.

11. Process for the treatment of glaucoma, which comprises applying to the eye of the patient a composition according to claim 10 in an amount which is effective for such treatment.

12. The process of claim 11 wherein said compound is applied at a concentration of 0.1–1% by weight in a pharmacologically acceptable liquid carrier.

13. An eye lotion for the treatment of glaucoma comprising a physiologically active amount of a compound of the formula

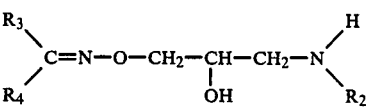

in which:
each of R$_3$ and R$_4$ is selected from hydrogen, and alkyl, alkenyl and cycloalkyl radicals, or R$_3$ and R$_4$ together with the carbon between them are a cycloalkylidene radical,
R$_2$ is a lower alkyl radical, and the salts thereof with opthalmologically acceptable acids, an opthalmologically acceptable liquid carrier, and an isotonic agent.

14. A lotion according to claim 13, in which said compound is 1-N-tert.-butylamino-3-(di-cyclopropyl-ketone-oximino)-propan-2-ol.

15. A lotion according to claim 13, in which said compound is 1-N-tert.-butylamino-3-(3,3,5-trimethyl-cyclohexane-1-oximino)-propan-2-ol.

16. A lotion according to claim 13, in which the active ingredient is present in amount of 0.1–1% by weight.

* * * * *